US012691289B2

(12) United States Patent
Doerr

(10) Patent No.: US 12,691,289 B2
(45) Date of Patent: Jul. 28, 2026

(54) IMPLANTABLE MEDICAL DEVICE, IMPLANT COMMUNICATION SYSTEM AND METHOD FOR TRANSFERRING DATA

(71) Applicant: BIOTRONIK SE & Co. KG, Berlin (DE)

(72) Inventor: Thomas Doerr, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 230 days.

(21) Appl. No.: 18/560,526

(22) PCT Filed: Jun. 2, 2022

(86) PCT No.: PCT/EP2022/065028
§ 371 (c)(1),
(2) Date: Nov. 13, 2023

(87) PCT Pub. No.: WO2022/268471
PCT Pub. Date: Dec. 29, 2022

(65) Prior Publication Data
US 2024/0252829 A1     Aug. 1, 2024

(30) Foreign Application Priority Data

Jun. 23, 2021     (EP) .................................... 21181017

(51) Int. Cl.
*A61N 1/37*          (2006.01)
*A61N 1/372*         (2006.01)
(52) U.S. Cl.
CPC ..... *A61N 1/37217* (2013.01); *A61N 1/37235* (2013.01); *A61N 1/37264* (2013.01); *A61N 1/37276* (2013.01)

(58) Field of Classification Search
CPC ............ A61N 1/37217; A61N 1/37235; A61N 1/37264; A61N 1/37276
See application file for complete search history.

(56) References Cited

U.S. PATENT DOCUMENTS

2016/0051825 A1*   2/2016   Ter-Petrosyan .... A61N 1/37247
                                                        607/60
2018/0028827 A1    2/2018   Schilling et al.
(Continued)

OTHER PUBLICATIONS

EP Search Report mailed on Dec. 17, 2021, by the European Patent Office for Application No. EP21181017.1. (6 pages).
(Continued)

*Primary Examiner* — Amanda K Hulbert
(74) *Attorney, Agent, or Firm* — Buchanan Ingersoll & Rooney PC

(57) ABSTRACT

The invention relates to an implantable medical device, in particular a diagnostic monitoring device, a pacemaker, a defibrillator and/or a neuro-stimulator, configured to exchange data with an external communication device, comprising a near-field telemetry interface), a first wireless communication interface operating in a frequency band reserved for medical implants, and a second wireless communication interface operating in a frequency band and/or using a communication protocol supported by consumer mobile communications devices, in particular smartphones and/or tablet computing devices. The invention further relates to an implant communication system and a method for transferring data between an implantable medical device and an external communication device. In addition, the invention relates to a computer program.

15 Claims, 2 Drawing Sheets

(56)  References Cited

U.S. PATENT DOCUMENTS

2018/0309766 A1    10/2018  Marnfeldt
2020/0306528 A1 *  10/2020  Linden ................. A61N 1/3752

OTHER PUBLICATIONS

International Search Report (PCT/ISA/210) and Written Opinion (PCT/ISA/237) mailed on Aug. 26, 2022, by the European Patent Office as the International Searching Authority for International Application No. PCT/EP2022/065028. (13 pages).

* cited by examiner

IMPLANTABLE MEDICAL DEVICE, IMPLANT COMMUNICATION SYSTEM AND METHOD FOR TRANSFERRING DATA

CROSS-REFERENCE TO RELATED APPLICATIONS

This application is the United States National Phase under 35 U.S.C. § 371 of PCT International Patent Application No. PCT/EP2022/065028, filed on Jun. 2, 2022, which claims the benefit of European Patent Application No. 21181017.1, filed on Jun. 23, 2021, the disclosures of which are hereby incorporated by reference herein in their entireties.

TECHNICAL FIELD

The present invention relates to an implantable medical device, in particular a diagnostic monitoring device, a pacemaker, a defibrillator and/or a neuro-stimulator, configured to exchange data with an external communication device. The present invention further relates to an implant communication system.

Moreover, the present invention relates to a computer implemented method for transferring data between an implantable medical device, in particular a diagnostic monitoring device, a pacemaker, a defibrillator and/or a neuro-stimulator, and an external communication device.

BACKGROUND

At present, active electronic implants are equipped with Bluetooth Low Energy (BLE) radios to enable communication with commercially available smartphones and tablets.

The solutions known to date with BLE radio usually still feature short-range telemetry as a telemetry option by means of an inductive communication interface. However, in the case of implants with a very long product life cycle/runtime, it is likely that compatibility with the respective commercially available communication infrastructures is no longer given at some point.

The product lifecycle of implantable active medical devices typically comprises three years of development, two years of approval, ten years of active sales and a further fifteen years of maintenance.

Therefore, in the case lack of compatibility with the respective commercially available communication infrastructures during the product lifecycle, the option of automatic, medium-range communication with the implant is no longer available and data can only be exchanged manually via the inductive communication interface.

The present disclosure is directed toward overcoming one or more of the above-mentioned problems, though not necessarily limited to embodiments that do.

SUMMARY

It is therefore an object of the present invention to provide an improved implantable medical device capable of connecting to existing communication infrastructures for at least part of their service life while maintaining basic communication functions throughout the product life cycle.

At least the object is solved by an implantable medical device, in particular a diagnostic monitoring device, a pacemaker, a defibrillator and/or a neuro-stimulator, configured to exchange data with an external communication device having the features of claim 1.

At least the object is furthermore solved by an implant communication system having the features of claim 10.

In addition, at least the object is solved by a computer implemented method for transferring data between an implantable medical device, in particular a diagnostic monitoring device, a pacemaker, a defibrillator and/or a neuro-stimulator, and an external communication device having the features of claim 13.

Moreover, at least the object is solved by a computer program of claim 15.

The present invention provides an implantable medical device, in particular a diagnostic monitoring device, a pacemaker, a defibrillator and/or a neuro-stimulator, configured to exchange data with an external communication device.

The implantable medical device comprises a near-field telemetry interface, a first wireless communication interface operating in a frequency band reserved for medical implants, and a second wireless communication interface operating in a frequency band and/or using a communication protocol supported by consumer mobile communications devices, in particular smartphones and/or tablet computing devices.

Furthermore, the present invention provides an implant communication system, comprising the implantable medical device according to the present invention, a programmer configured to communicate with the implantable medical device using inductive communication or medical RF communication, and a consumer mobile communication device, in particular a smartphone or tablet computing device, configured to communicate with the implantable medical device in a frequency band and/or using a communication protocol supported by the consumer mobile communication device.

Moreover, the present invention provides a computer implemented method for transferring data between an implantable medical device, in particular a diagnostic monitoring device, a pacemaker, a defibrillator and/or a neuro-stimulator, and an external communication device.

The method comprises the steps of providing a near-field telemetry interface, providing a first wireless communication interface operating in a frequency band reserved for medical implants, and providing a second wireless communication interface operating in a frequency band and/or using a communication protocol supported by consumer mobile communications devices, in particular smartphones and/or tablet computing devices.

In addition, the present invention provides a computer program with program code to perform the method according to the present invention when the computer program is executed on a computer.

The implantable medical device can be a diagnostic and/or therapeutic medical device such as a heart monitor, a diagnostic monitoring device, a pacemaker, a defibrillator and/or a neuro-stimulator.

It is an idea of the present invention to provide an implantable medical device with a very long product life cycle that can be integrated into generally available network infrastructures over a certain period of the life cycle without possibly losing the advantage of automatic radio telemetry over the entire life cycle.

Said automatic radio telemetry is maintained over the product life cycle of the implantable medical device by providing the first wireless communication interface operating in a frequency band reserved for medical implants, and the second wireless communication interface operating in a frequency band and/or using a communication protocol supported by consumer mobile communications devices, in particular smartphones and/or tablet computing devices.

A further advantage of providing multiple communication interfaces is that certain patient critical firmware functions of the implantable medical device can be programmed to be accessible by only one of the communication interfaces, namely the one that offers the highest level of security whereas the other communication interfaces provide the advantage of ease of use and interacting with the implantable medical device through any commercially available mobile communication device.

According to an aspect of the present invention, a communication range of the near-field telemetry is 2 to 50 cm, wherein a communication range of the first wireless communication interface is 50 cm to 10 m, in particular without signal reflection, and wherein a communication range of the second wireless communication interface is 50 cm to 100 m. Thus, the communication interfaces of the implantable medical device cover a wide range of usable communication ranges.

According to a further aspect of the present invention, the near-field telemetry interface is an inductive communication interface. This type of communication interface is used during initial setup and aftercare of the implantable medical device by a medical practitioner.

According to a further aspect of the present invention, the first wireless communication interface operates in the MICS band. The advantage of the MICS band is that enables wireless communication between the implantable medical device and an external communication device within the same room or building the patient is located in, i.e., is suitable for automatic communication and/or updates of the implantable medical device without the need of a medical practitioner to be on site.

According to a further aspect of the present invention, the second wireless communication interface is a Bluetooth, Bluetooth Low Energy and/or Bluetooth Mesh radio. The usage of Bluetooth advantageously enables a straightforward interaction medical device by the end user, i.e., the patient, by means of any commercially available mobile device such as a smart phone and/or tablet computing device.

According to a further aspect of the present invention, the implantable medical device is configured to allow access to a patient critical firmware function, in particular execution or setting of parameters of the patient critical firmware function, only via the near-field telemetry interface and/or the first wireless communication interface. Patient-critical firmware functions such as Brady_OFF_Mode, Therapy_OFF_State, or similar of implants, e.g., ICDs, S-ICD, IPGs, iLPs, or similar active implants are thus protected from unintended execution due to internal firmware errors and/or misuse by cyberattacks.

According to a further aspect of the present invention, the implantable medical device is configured to allow access to the patient critical firmware function upon authentication of the first wireless communication interface through a key exchange via near-field telemetry. This ensures access to the implantable medical device by only authorized users.

According to a further aspect of the present invention, the second wireless communication interface uses an authentication and/or data encryption method supported by consumer mobile communications devices, in particular smartphones and/or tablet computing devices. This enables ease of use with secure data transmission between the implantable medical device and a consumer mobile communication device such as a smart phone and/or a tablet computing device.

According to a further aspect of the present invention, the second wireless communication interface is configured to be switched off and/or de-energized by a control unit of the implantable medical device. This is advantages in case the communication protocol of the second wireless communication interface is no longer supported by consumer mobile communication devices.

According to a further aspect of the present invention, the programmer and/or the consumer mobile communication device is further configured to communicate with a cloud-based information management system. This advantageously enables automatic data transfer between cloud-based software applications and the implantable medical device via the programmer and/or the consumer mobile communication device.

According to a further aspect of the present invention, the implant communication system comprises a further medical RF communication device configured to communicate with the implantable medical device using MICS-band communication, wherein the further medical RF communication device is configured to communicate with a cloud-based information management system. The further medical RF communication device advantageously enables the maintenance of automatic data transfers between the implantable medical device and the cloud-based information management system in the case where the second wireless communication interface operating in a frequency band and/or using a communication protocol supported by consumer mobile communications devices, in particular smartphones and/or tablet computing devices is no longer supported and/or available.

According to a further aspect of the present invention, data is transferred from the implantable medical device to a cloud-based information management system via at least one of a programmer communicating with the implantable medical device using inductive communication or medical RF communication, and a consumer mobile communication device, in particular a smartphone or tablet computing device, communicating with the implantable medical device in a frequency band and/or using a communication protocol supported by the consumer mobile communication device.

That way, data transfer between the implantable medical device and an external communications device is ensured over the entire product life cycle of the implantable medical device.

The herein described features of the implantable medical device configured to exchange data with an external communication device are also disclosed for the computer implemented method for transferring data between an implantable medical device and an external communication device and vice versa.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

For a more complete understanding of the present invention and advantages thereof, reference is now made to the following description taken in conjunction with the accompanying drawings. The present invention is explained in more detail below using exemplary embodiments, which are specified in the schematic figures of the drawings, in which.

DETAILED DESCRIPTION

Figure 1:
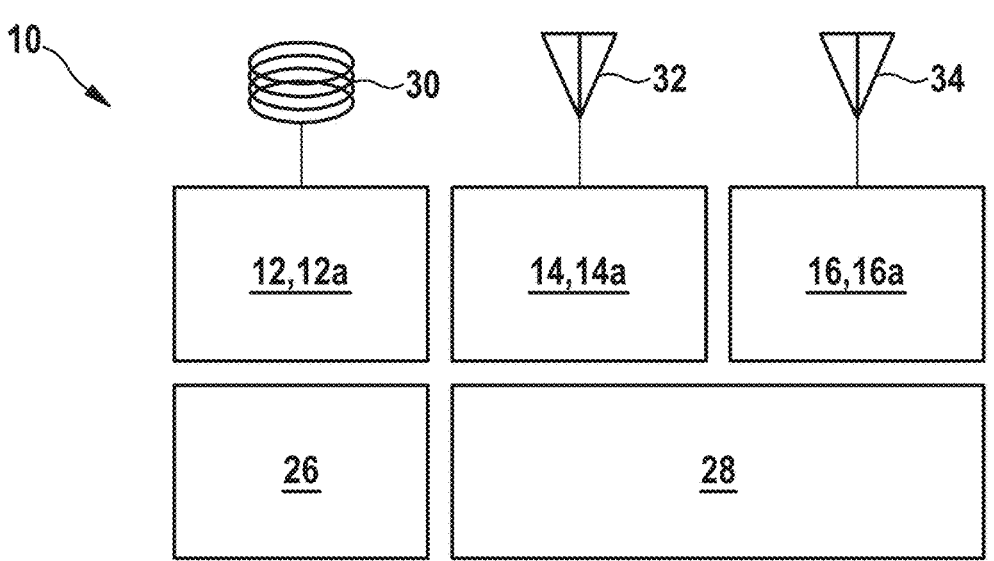
FIG. 1 shows a schematic view of an implantable medical device configured to exchange data with an external communication device according to a preferred embodiment of the present invention.

The implantable medical device 10 of FIG. 1, in particular a diagnostic monitoring device, a pacemaker, a defibrillator and/or a neuro-stimulator, is configured to exchange data D with an external communication device. To this end, the implantable medical device comprises a near-field telemetry interface 12 comprising an inductive near-field communication unit 12*a* connected to a corresponding communication coil 30.

The communication coil 30 operates in a relatively low frequency range of 30 kHz to 120 kHz. This allows the communication coil 30 to be housed within a metallic housing formed of titanium or stainless steel of the implantable medical device 10 without the housing excessively attenuating these frequencies.

The associated external communication device, in particular the programmer 18 (not shown in FIG. 1) also comprises a communication unit and a coil that operates in the same frequency range of the implant. Thus, bidirectional communication can be performed in the overall system.

Due to the low frequencies, the communication range is limited to typically 5 cm-25 cm. This ensures that communication can only take place if the external device is very close to the patient and thus the patient can perceive that such communication is taking place. Alternatively, standardized NFC technology can be used.

The implantable medical device 10 further comprises a first wireless communication interface 14 operating in a frequency band reserved for medical implants comprising a first radio telemetry unit 14*a* connected to a first antenna 32.

In addition, the implantable medical device 10 comprises a second wireless communication interface 16 operating in a frequency band and/or using a communication protocol supported by consumer mobile communications devices, in particular smartphones and/or tablet computing devices comprising a second radio telemetry unit 16*a* connected to a second antenna 34.

The implantable medical device 10 further comprises a power source 26 and a control unit 28 for controlling therapy and communication functions.

A communication range of the near-field telemetry is 2 to 50 cm. Furthermore, a communication range of the first wireless communication interface 14 is 50 cm to 10 m, in particular without signal reflection. Moreover, a communication range of the second wireless communication interface 16 is 50 cm to 100 m.

The near-field telemetry interface 12 is an inductive communication interface. The first wireless communication interface 14 operates in the MICS band and the second wireless communication interface 16 is a Bluetooth, Bluetooth Low Energy and/or Bluetooth Mesh radio.

The implantable medical device 10 is configured to allow access to a patient critical firmware function, in particular execution or setting of parameters of the patient critical firmware function, only via the near-field telemetry interface 12 and/or the first wireless communication interface 14.

Moreover, the implantable medical device 10 is configured to allow access to the patient critical firmware function upon authentication of the first wireless communication interface 14 through a key exchange via near-field telemetry.

The second wireless communication interface 16 uses an authentication and/or data encryption method supported by consumer mobile communications devices, in particular smartphones and/or tablet computing devices. The second wireless communication interface 16 is further configured to be switched off and/or de-energized by a control unit of the implantable medical device 10.

Figure 2:
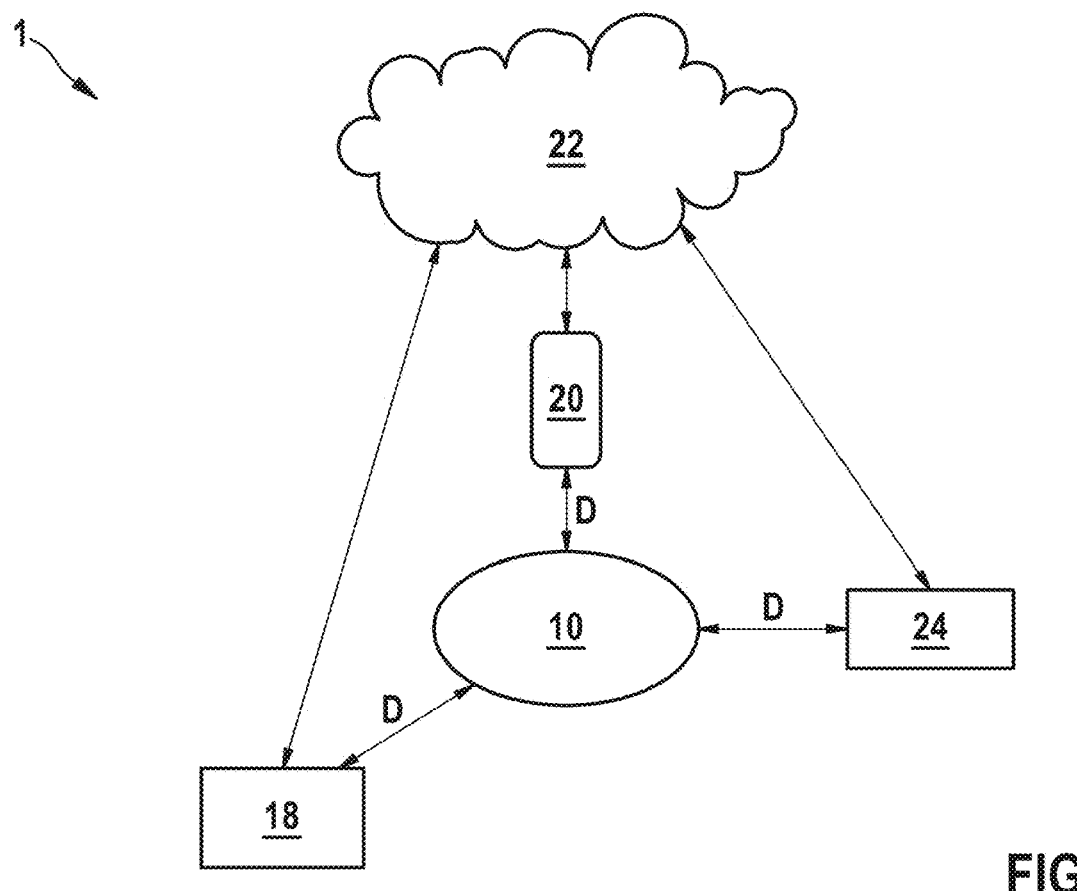
FIG. 2 shows a schematic view of an implant communication system according to the preferred embodiment of the present invention.

FIG. 2 shows a schematic view of an implant communication system according to the preferred embodiment of the present invention.

The implant communication system 1, comprises the implantable medical device 10, a programmer 18 configured to communicate with the implantable medical device 10 using inductive communication or medical RF communication, and a consumer mobile communication device 20, in particular a smartphone or tablet computing device, configured to communicate with the implantable medical device 10 in a frequency band and/or using a communication protocol supported by the consumer mobile communication device 20.

This makes it possible to display data directly on the smartphone and/or forward it to the cloud-based information management system 22 without the need for another external device.

The programmer 18 and/or the consumer mobile communication device 20 is further configured to communicate with a cloud-based information management system 22.

The implant communication system moreover comprises a further medical RF communication device 24 configured to communicate with the implantable medical device 10 using MICS-band communication. This is advantageous if, in the course of the very long product life cycle of the implantable medical device 10, compatibility with commercially available smartphones or tablets via BLE is no longer given.

In such a case, the alternative MICS-based wireless communication interface can be used to contact an external device 24 that can establish the connection between the implant and the cloud-based information management system 22.

Figure 3:
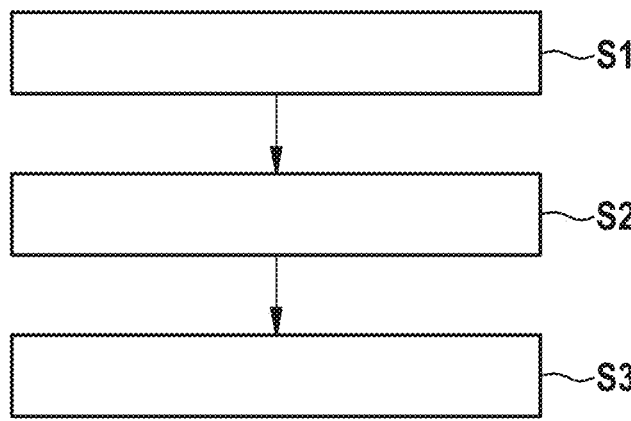
FIG. 3 shows a flowchart of a computer implemented method for transferring data between an implantable medical device and an external communication device according to the preferred embodiment of the present invention.

FIG. 3 shows a flowchart of a computer implemented method for transferring data D between an implantable medical device and an external communication device according to the preferred embodiment of the present invention.

The method comprises the step of providing S1 a near-field telemetry interface 12. Furthermore, the method comprises providing S2 a first wireless communication interface 14 operating in a frequency band reserved for medical implants. In addition, the method comprises providing S3 a second wireless communication interface 16 operating in a frequency band and/or using a communication protocol supported by consumer mobile communications devices, in particular smartphones and/or tablet computing devices.

Data D is transferred from the implantable medical device 10 to a cloud-based information management system 22 via at least one of a programmer 18 communicating with the implantable medical device 10 using inductive communication or medical RF communication, and a consumer mobile communication device 20, in particular a smartphone or tablet computing device, communicating with the implantable medical device 10 in a frequency band and/or using a communication protocol supported by the consumer mobile communication device 20.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

FURTHER EMBODIMENTS

A computer implemented method for transferring data between a medical device, in particular a diagnostic monitoring device, a pacemaker, a defibrillator and/or a neurostimulator, implanted into the human or animal body, and an external communication device, comprising the steps of providing a near-field telemetry interface, providing a first wireless communication interface operating in a frequency band reserved for medical implants, and providing a second wireless communication interface operating in a frequency band and/or using a communication protocol supported by consumer mobile communications devices, in particular smartphones and/or tablet computing devices.

REFERENCE SIGNS 1 system
10 implantable medical device
12 near-field telemetry interface
12a inductive near-field communication unit
14 first wireless communication interface
14a first radio telemetry unit
16 second wireless communication interface
16a second radio telemetry unit
18 programmer
20 consumer mobile communication device
22 cloud-based information management system
24 further medical RF communication device
26 power source
28 control unit
30 communication coil
32 first antenna
34 second antenna
D data
S1-S3 method steps

The invention claimed is:

1. Implantable medical device, configured to exchange data with an external communication device, comprising:
   a near-field telemetry interface;
   a first wireless communication interface operating in a frequency band reserved for medical implants; and
   a second wireless communication interface operating in a frequency band and/or using a communication protocol supported by consumer mobile communications devices.

2. Implantable medical device of claim 1, wherein a communication range of the near-field telemetry is 2 to 50 cm, wherein a communication range of the first wireless communication interface is 50 cm to 10 m, and wherein a communication range of the second wireless communication interface is 50 cm to 100 m.

3. Implantable medical device of claim 1, wherein the near-field telemetry interface is an inductive communication interface.

4. Implantable medical device of claim 1, wherein the first wireless communication interface operates in the MICS band.

5. Implantable medical device of claim 1, wherein the second wireless communication interface is a Bluetooth, Bluetooth Low Energy and/or Bluetooth Mesh radio.

6. Implantable medical device of claim 1, wherein the implantable medical device is configured to allow access to a patient critical firmware function only via the near-field telemetry interface and/or the first wireless communication interface.

7. Implantable medical device of claim 6, wherein the implantable medical device is configured to allow access to the patient critical firmware function upon authentication of the first wireless communication interface through a key exchange via near-field telemetry.

8. Implantable medical device of claim 1, wherein the second wireless communication interface uses an authentication and/or data encryption method supported by consumer mobile communications devices.

9. Implantable medical device of claim 1, wherein the second wireless communication interface is configured to be switched off and/or de-energized by a control unit of the implantable medical device.

10. Implant communication system, comprising:
    the implantable medical device of claim 1;
    a programmer configured to communicate with the implantable medical device using inductive communication or medical RF communication; and
    a consumer mobile communication device configured to communicate with the implantable medical device in a frequency band and/or using a communication protocol supported by the consumer mobile communication device.

11. Implant communication system of claim 10, wherein the programmer and/or the consumer mobile communication device is further configured to communicate with a cloud-based information management system.

12. Implant communication system of claim 10, comprising a further medical RF communication device configured to communicate with the implantable medical device using MICS-band communication, wherein the further medical RF communication device is configured to communicate with a cloud-based information management system.

13. Computer implemented method for transferring data comprising the steps of:
    exchanging data between an implantable medical device and an external communication device while both the implantable medical device and the external communication are operating within a communication network environment including a near-field telemetry interface, a first wireless communication interface operating in a frequency band reserved for medical implants, and a second wireless communication interface operating in a frequency band and/or using a communication protocol supported by consumer mobile communications devices.

14. Computer implemented method of claim 13, wherein data is transferred from the implantable medical device to a cloud-based information management system via at least one of:

a programmer communicating with the implantable medical device using inductive communication or medical RF communication; and a consumer mobile communication device communicating with the implantable medical device in a frequency band and/or using a communication protocol supported by the consumer mobile communication device.

15. Computer program with program code to perform the method of claim 13 when the computer program is executed on a computer.

* * * * *